US012564470B2

(12) United States Patent
Lavallée et al.

(10) Patent No.: US 12,564,470 B2
(45) Date of Patent: Mar. 3, 2026

(54) TRACKING ASSEMBLY FOR A SURGICAL ROBOTIC SYSTEM

(71) Applicant: ECENTIAL ROBOTICS, Gieres (FR)

(72) Inventors: Stéphane Lavallée, Saint-Martin-d'Uriage (FR); David Armand, Saint Egreve (FR); Lucas Michel, Sainte Agnes (FR)

(73) Assignee: ECENTIAL ROBOTICS, Gieres (FR)

( * ) Notice: Subject to any disclaimer, the term of this patent is extended or adjusted under 35 U.S.C. 154(b) by 401 days.

(21) Appl. No.: 18/019,904

(22) PCT Filed: Sep. 1, 2021

(86) PCT No.: PCT/EP2021/074193
§ 371 (c)(1),
(2) Date: Feb. 6, 2023

(87) PCT Pub. No.: WO2022/049164
PCT Pub. Date: Mar. 10, 2022

(65) Prior Publication Data
US 2023/0277271 A1     Sep. 7, 2023

(30) Foreign Application Priority Data

Sep. 2, 2020     (EP) ..................................... 20305974

(51) Int. Cl.
*A61B 90/11*     (2016.01)
*A61B 17/17*     (2006.01)
(Continued)

(52) U.S. Cl.
CPC .............. *A61B 90/11* (2016.02); *A61B 17/17* (2013.01); *A61B 34/30* (2016.02); *A61B 90/39* (2016.02);
(Continued)

(58) Field of Classification Search
CPC ......... A61B 90/11; A61B 90/39; A61B 90/50; A61B 2090/3937; A61B 2090/3945;
(Continued)

(56) References Cited

U.S. PATENT DOCUMENTS 11,096,709 B1 *   8/2021   Chin .............. A61B 17/320016
2013/0051059 A1 *   2/2013   Abai ........................ B60Q 1/28
362/240

(Continued)

FOREIGN PATENT DOCUMENTS

WO     2017208186 A2     12/2017
WO     2017208186 A3     12/2017

OTHER PUBLICATIONS

International Search Report in related PCT Application No. PCT/EP2021/074193, mailed Nov. 17, 2021.
(Continued)

*Primary Examiner* — Nhi Q Bui
(74) *Attorney, Agent, or Firm* — Thomas | Horstemeyer, LLP

(57) ABSTRACT

The invention relates to a tracking assembly (1) for a surgical robotic system, comprising at least two tracking patterns, wherein at least one of said at least two tracking patterns is adapted to be rotatably mounted relative to a tool guide (2) of the surgical GT robotic system so as to be moveable in rotation around a tool guide axis (X) normal to a reference plane (P), wherein each of said at least two tracking patterns defines a range of visibility substantially directed along a visibility axis, wherein an inclination relative to the reference plane (P) of the visibility axis of a first tracking pattern of the tracking assembly (1) is different from an inclination relative to the reference plane (P) of the visibility axis of a second tracking pattern of the tracking assembly (1).

14 Claims, 7 Drawing Sheets

(51) Int. Cl.
    *A61B 34/30*        (2016.01)
    *A61B 90/00*        (2016.01)
    *B25J 9/16*         (2006.01)

(52) U.S. Cl.
    CPC ........... *B25J 9/1692* (2013.01); *B25J 9/1697*
        (2013.01); *A61B 2090/3937* (2016.02); *A61B*
               *2090/3945* (2016.02)

(58) Field of Classification Search
    CPC ...... A61B 2090/376; A61B 2090/3983; A61B
              2090/0818; A61B 2090/034; A61B
              17/1703; A61B 17/1757; A61B 17/17;
              A61B 34/20; A61B 34/32; A61B
             34/2055; A61B 34/30; A61B 2017/00469;
              B25J 9/1692; B25J 9/1697
    See application file for complete search history.

(56)               References Cited

U.S. PATENT DOCUMENTS

| | | | |
|---|---|---|---|
| 2016/0278875 A1* | 9/2016 | Crawford | ............... A61B 90/98 |
| 2017/0252114 A1 | 9/2017 | Crawford | |
| 2018/0014888 A1 | 1/2018 | Bonny | |
| 2019/0290297 A1 | 9/2019 | Haider | |
| 2021/0030479 A1* | 2/2021 | Marti | ..................... A61B 34/20 |
| 2021/0323163 A1* | 10/2021 | Halvorsen | ............ G05B 19/401 |

OTHER PUBLICATIONS

European Extended Search Report in related EP Application No. 20305974.6, mailed Mar. 19, 2021.

\* cited by examiner

TRACKING ASSEMBLY FOR A SURGICAL ROBOTIC SYSTEM

CROSS REFERENCE TO RELATED APPLICATIONS

This application is the 35 U.S.C. § 371 national stage application of PCT Application No. PCT/EP2021/074193, filed Sep. 1, 2021, which application claims the benefit of European Application No. EP 20305974.6 filed Sep. 2, 2020, both of which are hereby incorporated by reference herein in their entireties.

The present invention relates to a tracking assembly allowing the localization, in terms of position and orientation, of a tool guide of a surgical robotic system.

GENERAL TECHNICAL FIELD AND PRIOR ART

Surgical robotic systems are frequently used during surgical interventions, in order to assist a surgeon. The surgical robotic system may guide the positioning and orientating of a surgical tool for the surgeon.

The surgical robotic system comprises a surgical robotic arm, comprising a distal end holding a tool guide. The tool guide is to be placed relative to a surgical target with a given position and orientation. Once the tool guide is placed relative to the surgical target, the surgeon can insert a surgical tool into the tool guide, so as to maneuver the surgical tool with the right position and orientation in order to proceed with the surgery. Alternatively, the tool guide can be used as a tool holder maintaining a tool relative to the robotic arm.

For example, in spine surgery, the user may have to implant one or several screws into one or several vertebrae. The tool guide is a drill guide, and the surgical target is a drilling axis in a vertebra. The surgeon can insert a handheld drill into the drill guide of the surgical robotic system, in order to drill a hole intended to receive the screw at the desired position and along the desired orientation. The tool guide allows positioning of the drill on the vertebra to be drilled, and maintains the drill at a desired orientation relative to the vertebra.

Several surgical targets can be defined in order to perform a surgical intervention. For example, the surgeon may have to place several screws in several different vertebrae of the patient or in a femoral neck or in a fractured bone.

Each of the surgical targets corresponds to a given position and orientation of the tool holder. Therefore, the surgical robotic system must be moved during surgery in order to sequentially place the tool holder relative to each of the defined surgical targets.

Surgical interventions using a surgical robotic system frequently rely on a fluoroscopy-based navigation of the surgical robotic system. In particular, X-ray fluoroscopy is frequently used to guide such surgical interventions.

X-ray fluoroscopy uses X-rays to produce an image of the inside of a patient's body in real time. X-ray fluoroscopy can provide a 2D image, or a 3D image obtained from multiple 2D images using tomography reconstruction algorithms. The fluoroscopic images can be intraoperatively acquired, so as to allow real-time navigation of the surgical robotic system during surgery.

In orthopedic, spine and traumatology surgery, fluoro-navigation based on X-ray fluoroscopy is frequently employed to monitor fracture reductions, to insert instruments at precise positions and orientations, and to position implants in one or several bone fragments.

In order to carry out fluoro-navigation, the surgical robotic system used during the surgical intervention must be localized in real-time. The surgical robotic system is thus equipped with a tracking assembly, such as an optical, electromagnetic, ultrasonic, or inertial tracking assembly. The tracking assembly is mounted on the surgical robotic system.

A localization system coupled to the tracking assembly allows the localization of the tracking assembly. The localization system is frequently an optical-based localization system, such as an infra-red camera. The camera detects and localizes, in terms of position and orientation, the tracking assembly.

The tracking assembly is localized relative to the tool guide using the localization system. The tool guide is localized relative to the surgical target using the localization system.

A known optical-based tracking assembly comprises several reflective markers, arranged in a tracking pattern. The reflective markers can be reflective disks mounted in recesses of the tracking assembly, or reflective spheres mounted at the end of pins extending from the tracking assembly. The reflective markers of the tracking assembly each possess a cone of visibility. All of the cones of visibility of the markers of a tracking pattern are oriented in the same direction.

The camera is adequately positioned before surgery, so that the whole area in which the surgical robotic system is likely to move during the surgical intervention is encompassed in the field of view of the camera.

The camera detects and localizes the tracking assembly mounted on the surgical robotic system, by detecting and localizing a tracking pattern of the tracking assembly.

In known tracking assemblies, in order for the camera to detect and localize a tracking pattern, two separate conditions must be met.

Firstly, each reflective marker of the tracking pattern needs to be imaged as a whole by the camera. In other words, in order to accurately detect and localize the reflective marker, the camera must see a perfect disk or sphere, and no part of the reflective marker should be hidden from the camera.

This first condition may not be met for certain positions and orientations of the tracking assembly, which can occur when the surgical robotic system is moved to certain positions and orientations during the surgical procedure. Indeed, the position and orientation of the tracking assembly varies during surgery, especially when several surgical targets, corresponding to several different positions and orientations of the tool holder, are defined for a surgical procedure.

For example, when the reflective markers are disks mounted in recesses of the tracking assembly, the shapes of the tracking assembly itself risk hiding part or all of the reflective disks from the camera in certain positions and orientations of the reflective assembly relative to the camera. When the reflective markers are spheres mounted on pins of the tracking assembly, the pin retaining the reflective spheres may hide part or all of the reflective spheres from the camera.

In order to meet this condition in a wider range of positions and orientations of the tracking assembly relative to the camera, parameters such as the shapes and volumes of the tracking assembly, the position and dimensions of the pins holding the markers, and the position of the tracking assembly on the surgical robotic system, are optimized in order to minimize obstruction by the pins and/or shapes of the tracking assembly to the reflective markers acquired by the camera.

Secondly, the camera must be correctly positioned and oriented relative to the tracking pattern to be detected and localized. In other words, in order to accurately detect and localize the tracking pattern, the camera must be positioned within the cone of visibility of each of the reflective markers of the tracking pattern. If the camera is outside the cone of visibility of one or several reflective markers, then the camera may not accurately detect and localize the tracking pattern.

As the surgical robotic system is moved into different positions and orientations during the surgical procedures, in order to reach several different surgical targets, the camera may become positioned outside the cone of visibility of at least one of the reflective markers of the tracking pattern to be detected and localized. The detection and localization of the reflective pattern is thus likely to be impeded, which makes the navigation of the surgical robotic system impossible. This leads to a security problem, as the surgical robotic system cannot be maneuvered in order to correctly position and orient the tool holder relative to the surgical target.

This second condition therefore restricts the number of allowable positions and orientations of the tracking assembly. The navigable work space of the surgical robotic system, that is to say the part of the absolute work space of the surgical robotic system in which the tool holder can be accurately tracked by the localization system, is thus restricted. Therefore, the surgical robotic system can be maneuvered towards only a limited number of surgical targets, without risking to remove the camera from the cone of visibility of at least one reflective marker of the tracking assembly.

Document US 2018/0014888 A1 discloses trackers fixed to the tool and freely rotating around a tool holder axis, in order to locate the tool axis. Document US 2017/0252114 A1 discloses trackers freely rotating around a tool holder axis, in order to improve the detection of the 3D position of a surgical tool. However, in both documents, the trackers can only be accurately detected and localized in a limited number of positions and orientations of the tool, that is to say in a restricted navigable work space of the tool holder. The number of surgical targets accessible to the tool is correspondingly restricted.

GENERAL PRESENTATION OF THE INVENTION

A general aim of the invention is to propose a tracking assembly improving the tracking of a surgical robotic system.

More particularly, an aim of the invention is to provide a tracking assembly allowing the surgical robotic system to be accurately tracked in more positions and/or orientations, that is to say in a greater navigable work space.

According to a first aspect, the invention is directed towards a tracking assembly for a surgical robotic system, the surgical robotic system comprising a tool guide extending substantially coaxially to a tool guide axis normal to a reference plane, the tracking assembly being adapted to be mounted on the surgical robotic system, wherein the tracking assembly comprises at least two tracking patterns, each tracking pattern comprising at least three optical markers, wherein at least one of said at least two tracking patterns is adapted to be rotatably mounted relative to the tool guide so as to be moveable in rotation around the tool guide axis, wherein each of said at least two tracking patterns defines a range of visibility associated to the tracking pattern, the range of visibility being substantially directed along a visibility axis, wherein an inclination relative to the reference plane of the visibility axis of a first tracking pattern of the tracking assembly is different from an inclination relative to the reference plane of the visibility axis of a second tracking pattern of the tracking assembly, wherein the tracking assembly is adapted to be detected and localized by a localization system when the localization system is within the range of visibility of at least one tracking pattern of the tracking assembly.

Some preferred but not limitative features of the tracking assembly described above are the following, taken individually or in combination:

Each optical marker is a reflective disk;

Each optical marker is a reflective sphere;

Each optical marker is an active marker;

The tracking assembly further comprises at least two additional tracking patterns, wherein each of said at least two additional tracking patterns defines a range of visibility associated to the respective additional tracking pattern, the range of visibility being substantially directed along a visibility axis, wherein an inclination relative to the reference plane of the visibility axis of a first additional tracking pattern of the tracking assembly is identical to an inclination relative to the reference plane of the visibility axis of a second additional tracking pattern of the tracking assembly, and wherein an orientation relative to the tool guide axis of the visibility axis of the first additional tracking pattern of the tracking assembly is different from an orientation relative to the tool guide axis of the visibility axis of the second additional tracking pattern of the tracking assembly.

According to a second aspect, the invention is directed towards a surgical robotic system, comprising:

a tracking assembly according to any one of claims 1 to 4;

a robotic arm comprising a tool guide extending substantially coaxially to the tool guide axis normal to the reference plane, the tracking assembly being adapted to be mounted on the robotic arm of the surgical robotic system.

Some preferred but not limitative features of the surgical robotic system described above are the following, taken individually or in combination:

The tool guide of the robotic arm is substantially in the shape of a hollow revolution cylinder extending around the tool guide axis, the tool guide comprising an outer wall and an inner wall, wherein the tracking assembly is adapted to be mounted on the outer wall of the tool guide so that all tracking patterns of the tracking assembly are movable in rotation around the tool guide axis, and wherein the inner wall of the tool guide is adapted to guide a translation of a surgical tool along the tool guide axis;

The tracking assembly comprises at least a first mounting surface and a second mounting surface, wherein the first mounting surface is adapted to be rotatably mounted relative to the tool guide so as to be moveable in rotation around the tool guide axis and the second mounting surface is adapted to be mounted in a fixed relation relative to the tool guide, and wherein each tracking pattern of the tracking assembly comprises at least one optical marker mounted on the first mounting surface and at least one optical marker mounted on the second mounting surface;

The surgical robotic system further comprises stabilization means adapted to maintain the tracking assembly in a given position and orientation relative to the tool guide in the absence of solicitation of the tracking assembly in rotation around the tool guide axis;

The surgical robotic system further comprises:

a reference tracking assembly, a localization system adapted to detect and localize the reference tracking assembly and the tracking assembly when the localization system is within a range of visibility of at least one tracking pattern of the tracking assembly, the localization system being adapted to determine a position and an orientation of the tracking assembly relative to a position and an orientation of the reference tracking assembly.

According to a third aspect, the invention is directed towards a method for aligning a tool guide of a surgical robotic system according to the second aspect with a surgical target axis, comprising the following steps:

S1: detecting and localizing, by the localization system:

(a) a reference tracking assembly attached to an anatomical structure in a determined fixed position and orientation relative to the surgical target axis, and (b) at least one tracking pattern of the tracking assembly, if necessary, by rotating at least one tracking pattern of the tracking assembly around the tool guide axis, S2: determining a position and/or orientation of the tool guide relative to the surgical target axis, based on the detection and localization of the tracking assembly relative to the reference tracking assembly performed in step S1 and on the position and orientation of the reference tracking assembly relative to the surgical target axis, S3: moving the robotic arm to adjust the position and/or orientation of the tool guide to align the tool guide axis with the surgical target axis.

The step S1 may comprise the following steps:

S11: acquiring an image by the localization system,

S12: if no tracking pattern is detected by the localization system on the basis of the acquired image, rotating at least one tracking pattern of the tracking assembly around the tool guide axis until the localization system detects at least one tracking pattern of the tracking assembly, S13: detecting and localizing at least one of the at least one detected tracking pattern of the tracking assembly by the localization system.

Rotating at least one tracking pattern of the tracking assembly around the tool guide axis may be performed manually by a user.

Rotating at least one tracking pattern of the tracking assembly around the tool guide axis may be performed automatically by motorization means, the motorization means being controlled according to the result of the detection of a tracking pattern by the localization system.

PRESENTATION OF THE FIGURES

Other features and advantages of the invention will emerge from the following description, which is purely illustrative and non-limiting and must be considered with respect to the appended figures in which.

DESCRIPTION OF SEVERAL EMBODIMENTS

Figure 1A:
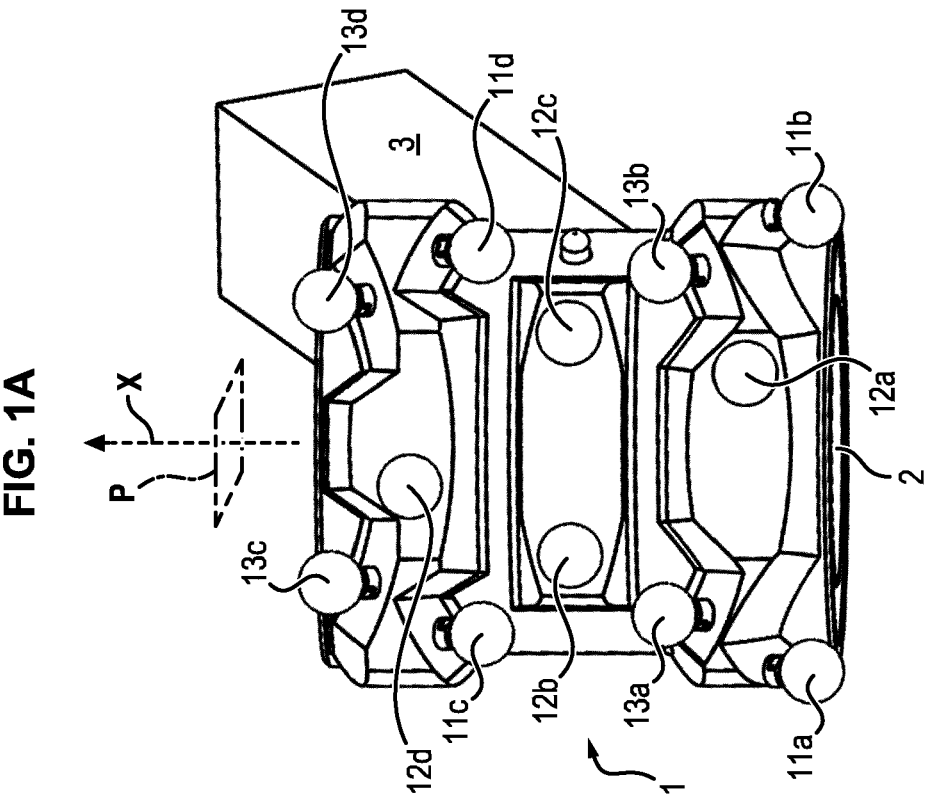
FIGS. 1a and 1b are perspective views of a tracking assembly according to an embodiment of the invention.

Examples of a tracking assembly 1 for a surgical robotic system are illustrated in FIGS. 1a to 4b. Examples of a surgical robotic system comprising a tracking assembly 1 are illustrated in FIGS. 5a to 6b.

The surgical robotic system comprises a tool guide 2 extending substantially coaxially to a tool guide axis X normal to a reference plane P. The tracking assembly 1 is adapted to be mounted on the surgical robotic system.

In the following description, the term "position" refers to 3D coordinates of a point in a Cartesian coordinate system. The term "orientation" refers to an angular orientation of an object around the tool guide axis X. The term "localization" refers to both the position and orientation of an object, such that an object is localized when both its position in a Cartesian coordinate system and its orientation relative to the tool guide axis X are determined.

The term "tool guide" is used to designate a device which is attached to a distal end of a surgical robotic device, more particularly to a distal end of a surgical robotic arm, and which allows maintaining a surgical tool along a guiding axis, or tool guide axis X.

The surgical tool may be movable relative to the tool guide 2 in rotation and/or translation about said guiding axis. In this case, the tool guide 2 comprises a tool channel into which the surgeon can insert the surgical tool in order to proceed to the surgery. The tool guide 2 may be placed with a given position and orientation such that when the surgeon inserts the surgical tool into the tool guide 2, the position and orientation of the surgical tool coincides with a defined surgical target. The tool guide 2 orients the surgical tool along the tool guide axis X so as to guide a translation of a surgical tool along the tool guide axis X. The position of the surgical tool along the tool guide axis X is controlled by the surgeon. The tool guide 2 may also contain a stop adapted to limit the depth of the surgical tool. Therefore, the user cannot insert the surgical tool deeper than a predetermined depth.

Alternatively, the surgical tool may be fixed to the tool guide 2; for example, the tool guide 2 may comprise a tool holder comprising a support and fastening means configured to rigidly fix the surgical tool to the support. Optionally, the tool guide 2 may also comprise one or more actuators adapted to move the tool holder and the surgical tool in translation and/or in rotation about the guiding axis relative to the surgical robotic device. The tool guide 2 may be placed with a given position and orientation such that the position and orientation of the surgical tool may coincide with a surgical target. Both the position and the orientation of the surgical tool along the tool guide axis X are controlled by the surgical robotic device and/or the actuator(s).

The tool guide 2 may be removably or permanently attached to the surgical robotic system.

A surgical target may be defined by a surgical target axis. The surgical target axis may correspond to a given surgical target axis position and/or orientation. Aligning the tool guide 2 with the surgical target axis corresponds to placing the tool guide 2 on the surgical target axis. In other words, when aligned, the position and/or orientation of the tool guide 2 correspond to the position and/or orientation of the surgical target axis. More particularly, the surgical target axis may correspond to a desired position and/or orientation of the tool guide axis X and of the surgical tool axis when the surgical tool is inserted in the tool channel, or fixed to the tool holder. For example, in the case where the surgical tool is a drill, the surgical target axis may correspond to the axis along which the hole is drilled.

The tracking assembly 1 comprises at least two tracking patterns, each tracking pattern comprising at least three optical markers 11*a*-13*d*.

At least one of said at least two tracking patterns is adapted to be rotatably mounted relative to the tool guide 2 so as to be moveable in rotation around the tool guide axis X. A tracking pattern adapted to be rotatably mounted relative to the tool guide 2 around the tool guide axis X is called a rotatable tracking pattern.

Each of said at least two tracking patterns defines a range of visibility associated to the tracking pattern, the range of visibility being substantially directed along a visibility axis X11, X12, X13, wherein an inclination relative to the reference plane P of the visibility axis X11, X12, X13 of a first tracking pattern of the tracking assembly 1 is different from an inclination relative to the reference plane P of the visibility axis X11, X12, X13 of a second tracking pattern of the tracking assembly 1.

The tracking assembly 1 is adapted to be detected and localized by a localization system 4 when the localization system 4 is within the range of visibility of at least one tracking pattern of the tracking assembly 1.

The localization system 4 may be a camera, more particularly an optical-based camera.

At least one tracking pattern of the tracking assembly 1 is a rotatable tracking pattern, that is to say is a tracking pattern which can rotate around the tool guide axis X. In other words, the orientation of the rotatable tracking assembly 1 relative to the tool guide axis X can be modified.

Therefore, if a movement of the surgical robotic system during the surgical intervention leads to the localization system 4 becoming outside of the range of visibility of all tracking patterns, then the at least one rotatable tracking pattern can be rotated around the tool guide axis X so that the localization system 4 may stay within the range of visibility of the at least one tracking pattern. The at least one rotating tracking pattern thus allows the tracking assembly 1 to be detected and localized by the localization system 4 in a wide range of positioning and orientating of the surgical robotic system in the reference plane P, that is to say around the tool guide axis X.

Furthermore, the tracking assembly 1 comprises at least two tracking patterns having ranges of visibility which have different inclinations relative to the reference plane P, the reference plane P being normal to the tool guide axis X. Therefore, if a movement of the surgical robotic system during the surgical intervention leads to the localization system 4 becoming outside of the range of visibility of the first (respectively second) tracking pattern, then the localization system 4 may as a result of the movement of the surgical robotic system become within the range of visibility of the second (respectively first) tracking pattern. The differently inclined tracking patterns thus allow the tracking assembly 1 to be detected and localized by the localization system 4 in a wide range of positions and orientations of the surgical robotic system, more particularly in a wide range of inclinations of the tool guide 2 relative to the reference plane P.

For example, if the surgical procedure necessitates the tool guide 2 to be successively placed with different inclinations relative to the localization system 4 in order to reach differently inclined surgical targets, the localization system 4 has greater probability to detect and localize at least one tracking pattern, among the two tracking patterns having different inclinations relative to the reference plane P.

Indeed, at least one tracking pattern can be correctly positioned and oriented with regard to the localization system 4 for a greater number of positions and orientations of the tracking assembly 1. In other words, the localization system 4 is kept within the range of visibility of at least one tracking pattern for a greater number of positions and orientations of the surgical robotic assembly.

Therefore, the tracking assembly 1 improves the tracking of the surgical robotic system on which it is mounted, as it can be accurately detected and localized in a wider range of positions and orientations of the surgical robotic system. As a result, the surgical robotic system can be accurately tracked in more positions and/or orientations, that is to say in a greater navigable work space. Therefore, a wider range of surgical targets can be reached by the surgical robotic system.

Furthermore, as the tracking assembly 1 comprises at least two tracking patterns, more than one tracking pattern may be detected and localized by the localization system 4. This is the case when the localization system 4 is within the range of visibility of two or more tracking patterns.

If the localization system 4 detects and localizes at least two tracking patterns, the localization system 4 may select the tracking pattern with the range of visibility leading to the more accurate detection and localization of the localization system 4, in order to deduce the localization of the tracking assembly 1.

Alternatively, the localization system 4 may detect and localize all tracking patterns, and compare the obtained localizations in order to improve their reliability. This way, the localization system 4 can detect a problem if one of the detected tracking patterns is out of calibration, for example if it is misplaced or displaced, or if its localization is flawed, for example due to dirt or blood partially covering the reflective markers. The resulting tracking accuracy will therefore not be reduced by an out of calibration or flawed tracking pattern, and the system can alert the user that the localization of a given tracking pattern is flawed. This redundancy improves the security of the localization, therefore of the surgical operation.

The tracking assembly 1 may comprise more than two tracking patterns, for example three tracking patterns. A greater number of tracking patterns further widens the navigable work space of the surgical robotic system comprising the tracking assembly 1.

More than one tracking pattern may be rotatably mounted relative to the tool guide 2 so as to be moveable in rotation around the tool guide axis X. Thus, the tracking assembly 1 may be localized by the localization system 4 in a wider number of positions and orientations of the surgical robotic system in the reference plane P, that is to say around the tool guide axis X.

For example, all of the tracking patterns of the tracking assembly 1 may be rotatably mounted relative to the tool guide 2 so as to be moveable in rotation around the tool guide axis X. The tracking assembly 1 as a whole can be rotated around the tool guide axis X, thus leading to a simultaneous and identical rotation of all of its tracking patterns around the tool guide axis X.

Each tracking pattern comprises at least three optical markers 11a-11d, 12a-12d, 13a-13d, in order to be accurately detected and localized, when the localization system 4 is within the range of visibility of the tracking pattern. The rotation of the rotatable tracking pattern may correspond to a simultaneous and identical rotation of each of its optical markers 11a-13d.

Each tracking pattern may comprise more than three optical markers 11a-13d, for example four or five optical markers 11a-13d. The number of optical markers 11a-13d of a tracking pattern is sufficient to allow a robust and accurate detection and localization of the tracking pattern by the localization system 4. A greater number of optical markers 11a-13d in a tracking pattern may increase the robustness and accuracy of the detection and localization of the tracking pattern. It may also allow detection and localization of the tracking pattern in more positions and orientations of the tracking pattern, as such detection and localization may be performed by detecting only three optical markers out of all the optical markers of the tracking pattern.

Each optical marker 11a-11d, 12a-12d, 13a-13d of a tracking pattern may define an optical marker range of visibility substantially directed along an optical marker visibility axis.

The optical marker range of visibility is a cone of visibility centered around the optical marker visibility axis and having a given angular aperture. The cone of visibility is due to several phenomena intrinsic to the construction of markers. In the case of passive reflective markers, they are constituted of micro spheres spread on a surface like in tape 3M 7610 for example, and the power of reflection of said marker decreases with the angle of visibility with respect to said surface. In the case of spherical retroreflective markers, the pin or post holding the sphere creates an error as soon as it is visible, which induces of loss of perfect visibility (with no loss of accuracy). The use of active LEDs may offer a wider cone of visibility but still remains much below an ideal half angle of 90° around the axis of said LED.

The optical markers 11a-13d may be mounted on the surgical robotic system such that all of the optical markers 11a-11d, 12a-12d, 13a-13d of a given tracking pattern are arranged coaxially. In other words, all of the optical marker visibility axes of the optical markers 11a-13d of a given tracking pattern are parallel. For example, in the case of optical markers 11a-13d defining cones of visibility, the optical markers 11a-13d may be mounted on the surgical robotic system such that all of the cones of visibility of the optical markers 11a-13d of a tracking pattern are oriented in the same direction.

When a given tracking pattern of the tracking assembly 1 comprises more than three optical markers 11a-13d, all of the optical markers 11a-13d of the given tracking pattern may be arranged in a same plane, said plane being normal to the optical marker visibility axes. Alternatively, three optical markers 11a-13d may define a first plane, and at least one optical marker may be arranged in a second plane which is parallel to and different from the first plane. This configuration where all the optical markers 11a-13d of a given tracking pattern are not coplanar increases the robustness and accuracy of the detection and localization of the tracking pattern.

The position and orientation of the optical markers 11a-13d of the tracking assembly may be optimized in order to prevent the hiding of an optical marker 11a-13d by another optical marker 11a-13d of the tracking assembly. Thus, the localization system 4 may detect each optical marker 11a-11d, 12a-12d, 13a-13d of a tracking pattern as a whole and at the same time.

The direction of the optical marker visibility axes of the optical markers 11a-13d of a given tracking pattern may correspond to the direction of the visibility axis X11, X12, X13 of the given tracking pattern.

The range of visibility of a given tracking pattern may correspond to an intersection of the ranges of visibility of at least three optical markers 11a-13d of the given tracking pattern. In other words, in order for the given tracking pattern to be detected and localized by the localization system 4, the localization system 4 must be simultaneously within the range of visibility of at least three optical markers 11a-13d of the given tracking pattern.

Alternatively, the range of visibility of a given tracking pattern may correspond to a combination of the ranges of visibility of the optical markers 11a-13d of the given tracking pattern. In other words, in order for the given tracking pattern to be detected and localized by the localization system 4, the localization system 4 must be within the range of visibility of at least one optical marker of the given tracking pattern.

Other alternatives for the determining the range of visibility of a given tracking pattern, based on the ranges of visibility of one or more optical markers 11a-13d of the given tracking pattern, may be envisaged.

Figure 1B:
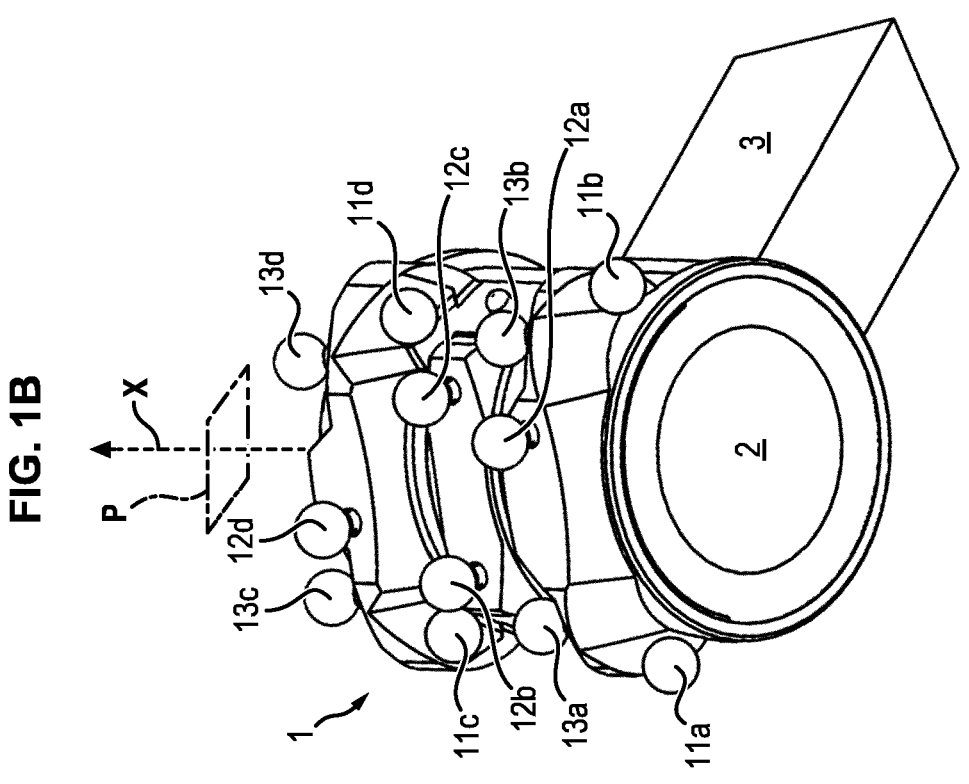
Figure 2:
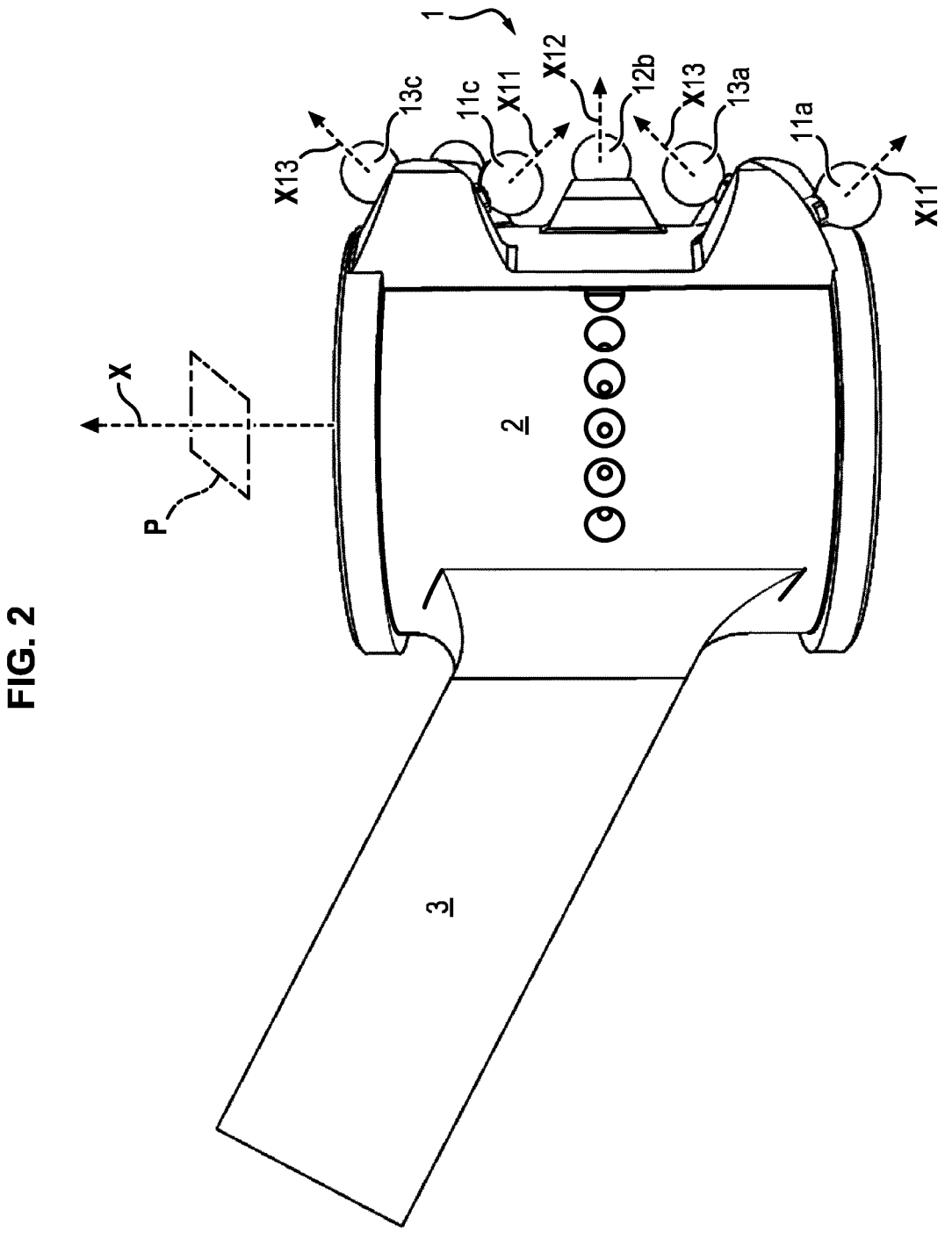
FIG. 2 is a side view of a tracking assembly according to an embodiment of the invention.

Each optical marker 11a-13d of a tracking pattern may be a reflective sphere. The cone of visibility of each optical marker 11a-13d may have an aperture comprised between 50° and 60°. The reflective sphere may be adapted to be mounted on an end of a rod, the rod extending along the reflective sphere visibility axis X11, X12, X13, the rod being mounted on the surgical robotic system. FIGS. 1a, 1b and 2 illustrate by way of example tracking assemblies 1 in which each optical marker 11a-13d is a reflective sphere.

Alternatively, each optical marker 11a-13d of a tracking pattern may be a reflective disk. The cone of visibility of each optical marker 11a-13d may have an aperture comprised between 40° and 50°. Each optical marker 11a-13d may be directly mounted on the surgical robotic system, for example the disks may be inserted into recesses of the surgical robotic system. FIGS. 3a, 3b, 3c, 4a and 4b illustrate by way of example tracking assemblies in which each optical marker 11a-13d is a reflective disk.

Alternatively, each optical marker 11a-13d of a tracking pattern may be an active marker such as a LED or a luminescent disc.

Alternatively, some optical markers 11a-13d can be reflective disks, and/or other can be reflective spheres, and/or other can be active markers such as a LEDs or luminescent discs.

The optical markers 11a-13d of a first tracking pattern may be intertwined with the optical markers 11a-13d of a second tracking pattern. More particularly, optical markers 11*a*-13*d* with different inclinations relative to the reference plane P may be mounted next to each other on the tracking assembly 1 such that the tracking patterns overlap each other.

Figure 3B:
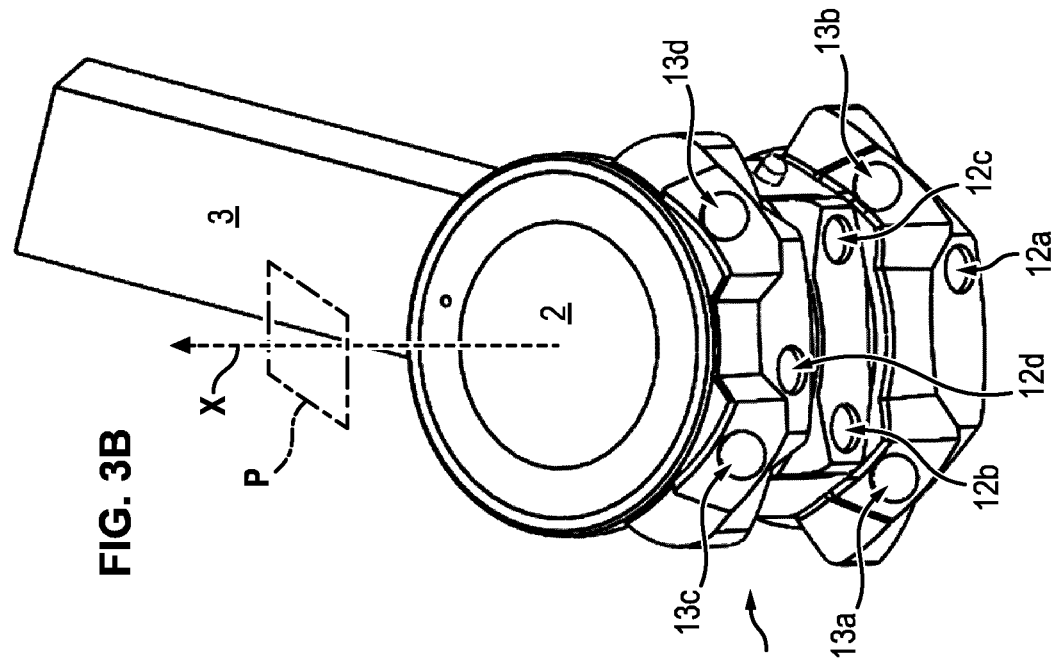
FIGS. 3a and 3b are perspective views of a tracking assembly according to another embodiment of the invention.
Figure 3A:
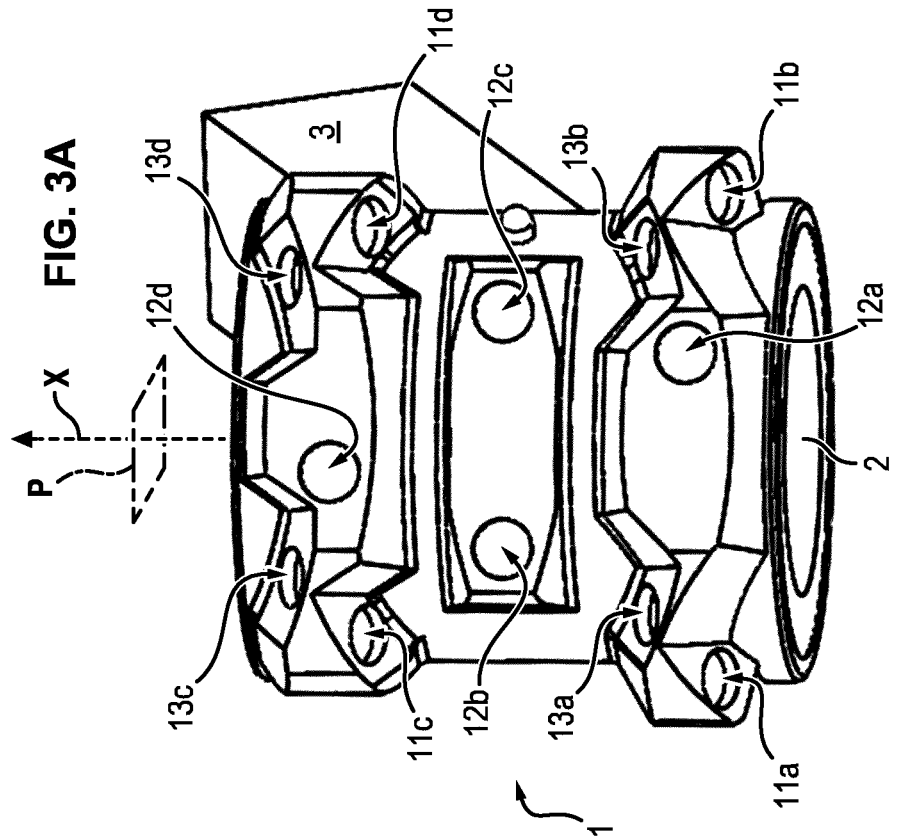
Figure 3C:
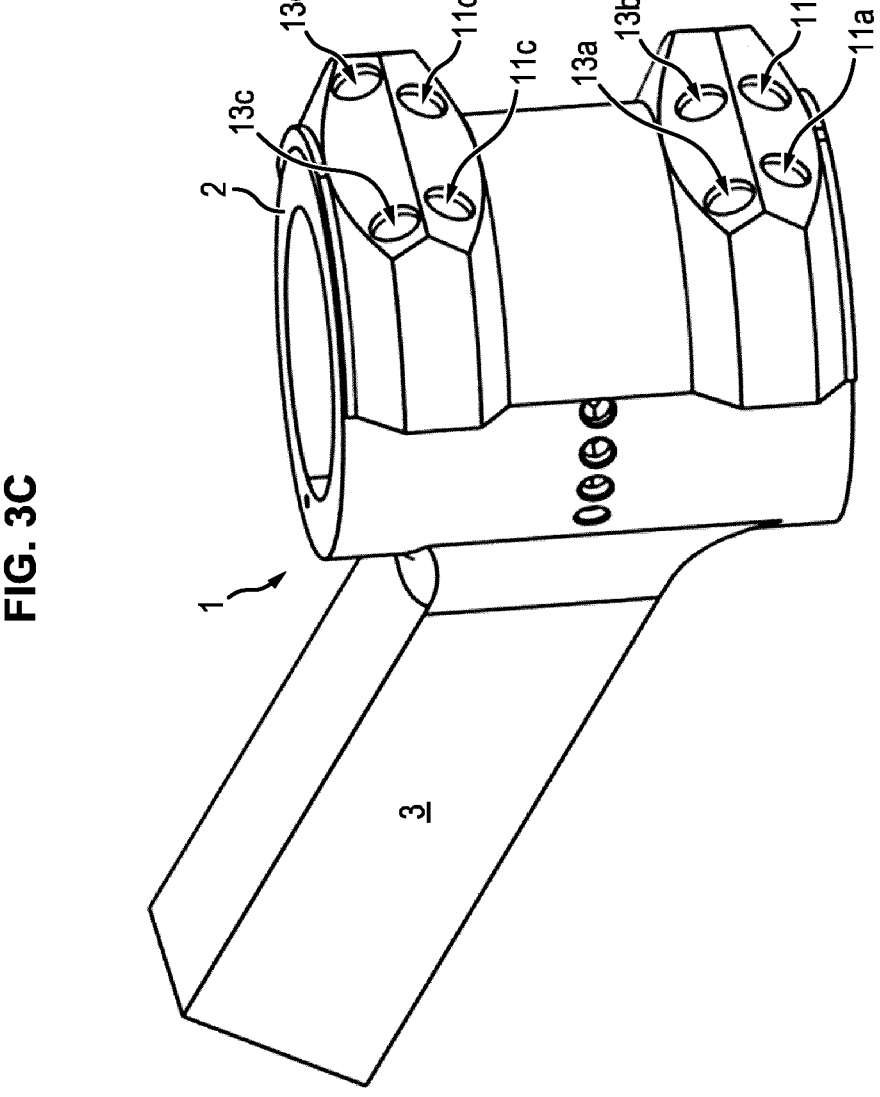
FIG. 3c is a perspective view of a tracking assembly according to another embodiment of the invention.

For example, the tracking assembly 1 illustrated in FIGS. 1*a*, 1*b*, 2, 3*a* and 3*b* comprises three tracking patterns, and the tracking assembly 1 illustrated in FIG. 3*c* comprises two tracking patterns. The tool guide 2 comprises a tool channel, and the tracking assembly 1 is mounted directly on the tool guide 2 of the surgical robotic system, on an external surface of the tool guide 2. The tracking assembly 1 as a whole is rotatable around the tool guide axis X. Each tracking pattern comprises four optical markers 11*a*-13*d*.

The term "inclination" is used to designate an angle formed between the visibility axis X11, X12, X13 and the reference plane P. The inclination of the visibility axis X11, X12, X13 relative to the reference plane P can be negative, positive, or equal to zero.

The inclinations of the visibility axes X11, X12, X13 of at least two tracking patterns of the tracking assembly 1 are different, any combination of said inclinations being possible. For example, both inclinations of the tracking patterns can be positive, one inclination being more positive than the other, both inclinations can be negative, one inclination being more negative than the other, one inclination can be positive while the other is equal to zero, or one inclination can be negative while the other is equal to zero.

For example, for markers having an aperture of 45°, the inclination of the visibility axis X11, X12, X13 of the first tracking pattern with respect to the reference plane P may make an angle of at least 70° relative to the inclination of the visibility axis X11, X12, X13 of the second tracking pattern with respect to the reference plane The angular value between the visibility axes is selected to ensure a continuous visibility of the tracker assembly between the two tracking patterns, preferably with an overlap. For example, for markers having an aperture of 45° and an angular value between the visibility axes of 70°, an overlap of 20° is offered. In the overlapping directions, both patterns are visible, which reinforces the accuracy of the system.

When the tracking assembly 1 comprises more than two tracking patterns, each of the tracking patterns defines a range of visibility associated to the tracking pattern and directed along a visibility axis X11, X12, X13.

Each of the visibility axes X11, X12, X13 may have different inclinations relative to the reference plane P. In other words, each tracking pattern of the tracking assembly 1 may define respective visibility axes X11, X12, X13 with a respective inclination relative to the reference plane P, the inclination of the visibility axis X11, X12, X13 of a tracking pattern being different to the inclination of the visibility axis X11, X12, X13 of another tracking pattern. Thus, the localization system 4 may be inside the range of visibility of at least one tracking pattern for a greater number of inclinations relative to the reference plane P of the tracking assembly 1, the navigable work space of the robotic arm 3 being therefore further enlarged.

Alternatively, two or more tracking patterns may have visibility axes X11, X12, X13 having a same inclination relative to the reference plane P. This configuration may provide greater redundancy, as the localization system 4 is thus more likely to localize at once all the tracking patterns having the same inclination.

In the tracking assembly 1 illustrated by way of example in FIGS. 1*a*, 1*b*, 2, 3*a* and 3*b*, each of the three tracking patterns define a range of visibility directed along a respective visibility axis X11, X12, X13. Each visibility axis X11,

X12, X13 of the three tracking patterns has an inclination relative to the reference plane P which is different from an inclination of another tracking pattern.

The visibility axis X11 of the tracking pattern comprising the four optical markers 11*a*-11*d* has a negative inclination relative to the reference plane P. The visibility axis X12 of the tracking pattern comprising the four optical markers 12*a*-12*d* has an inclination equal to 0° relative to the reference plane P. The visibility axis X13 of the tracking pattern comprising the four optical markers 13*a*-13*d* has a positive inclination relative to the reference plane P.

The tracking assembly 1 may further comprise at least two additional tracking patterns, preferably at least two additional optical tracking patterns. Each of said at least two additional tracking patterns comprises at least three optical markers, and defines a range of visibility associated to the respective additional tracking pattern, the range of visibility being substantially directed along a visibility axis.

An inclination relative to the reference plane P of the visibility axis of a first additional tracking pattern of the tracking assembly 1 is identical to an inclination relative to the reference plane P of the visibility axis of a second additional tracking pattern of the tracking assembly 1. An orientation relative to the tool guide axis X of the visibility axis of the first additional tracking pattern of the tracking assembly 1 is different from an orientation relative to the tool guide axis X of the visibility axis of the second additional tracking pattern of the tracking assembly 1.

In other words, the additional tracking patterns have the same inclination relative to the reference plane P, and have different orientations relative to the tool guide axis X. Therefore, such additional tracking patterns further increase the range of positions and orientations for which the surgical robotic system can be localized, both around the tool guide axis X, and in a perpendicular orientation relative to the tool guide axis X. For example, the tracking assembly 1 may comprise two or more additional tracking patterns having an inclination relative to the reference plane P equal to zero, and oriented differently relative to the tool guide axis X.

A surgical robotic system, illustrated by way of example in FIGS. 5*a* to 6*b*, may comprise:

a tracking assembly 1 as described above;

a robotic arm 3 comprising a tool guide 2 extending substantially coaxially to the tool guide axis X normal to the reference plane P, the tracking assembly 1 being adapted to be mounted on the robotic arm 3 of the surgical robotic system.

At least one tracking pattern of the tracking assembly 1 is adapted to be rotatably mounted relative to the tool guide 2 of the robotic arm 3 so as to be moveable in rotation around the tool guide axis X.

The tool guide 2 may be positioned at a distal end of the robotic arm 3, the tool guide 2 forming an end-effector of the robotic arm 3. The tool guide 2 may be integral with the robotic arm 3, or may be mounted on the robotic arm 3 of the surgical robotic system.

The tracking assembly may be adapted to be mounted directly on the tool guide 2, or on the robotic arm 3 of the surgical robotic system.

In a first embodiment illustrated by way of example in FIGS. 1*a*-3*b*, the tool guide 2 of the robotic arm 3 is substantially in the shape of a hollow revolution cylinder extending around the tool guide axis X. The tool guide 2 comprises an outer wall and an inner wall. The tracking assembly 1 may be adapted to be mounted on the outer wall of the tool guide 2 so that all tracking patterns of the tracking assembly 1 are movable in rotation around the tool guide axis X.

The inner wall of the tool guide 2 may be a cylindrical inner wall adapted to guide a translation of a surgical tool along the tool guide axis X.

In this first embodiment, the tracking patterns are mounted directly on the tool guide 2, which comprises a tool channel into which the surgical tool can be inserted. Alternatively, the tool guide 2 could comprise fastening means and position control means adapted to fix and guide a surgical tool, the tool guide 2 being a tool holder.

The tool guide 2 may comprise a distal extremity adapted to be close to or in contact with the patient's skin during surgery, and a proximal extremity opposed to the distal extremity. The optical markers 11*a*-13*d* of the tracking patterns may be mounted on the outer wall of the tool guide 2 between the distal extremity and the proximal extremity, in an intertwined manner.

The outer wall of the tool guide 2 may comprise several substantially plane faces having different inclinations relative to the reference plane P. The optical markers 11*a*-13*d* may be mounted directly on the faces of the outer wall of the tool guide 2, so that the optical markers visibility axes are perpendicular to the faces on which the optical markers 11*a*-13*d* are mounted. The inclinations of the faces of the outer wall of the tool guide 2 relative to the reference plane P may correspond to the inclinations of the visibility axes X11, X12, X13 of the tracking patterns.

Figures 4A, 4B:
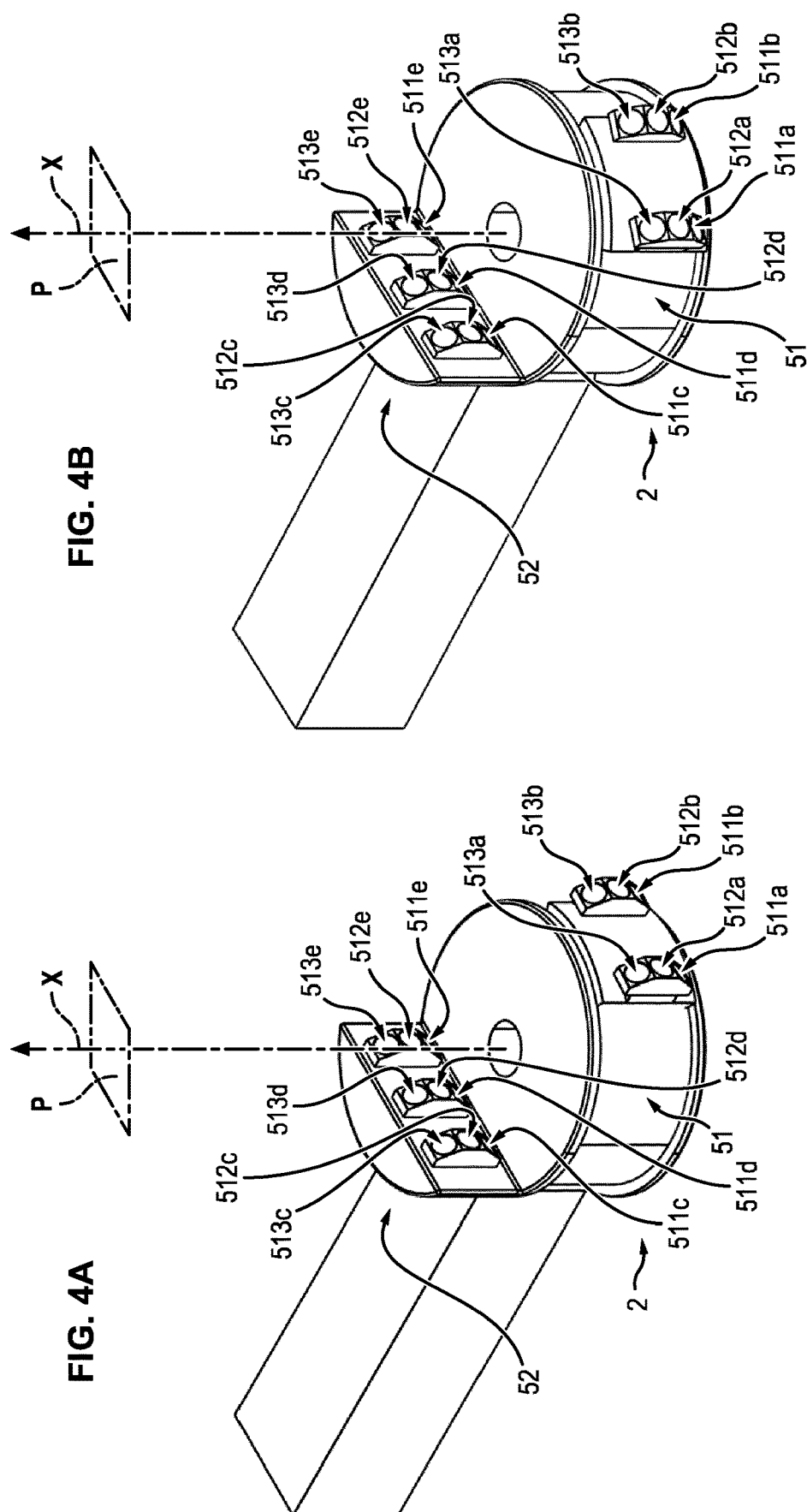
FIGS. 4a and 4b are perspective views of a tracking assembly according to another embodiment of the invention.

In a second embodiment, illustrated by way of example in FIGS. 4*a* and 4*b*, the tracking assembly 1 comprises at least a first mounting surface 51 and a second mounting surface 52.

The first mounting surface 51 may be adapted to be rotatably mounted relative to the tool guide 2 so as to be moveable in rotation around the tool guide axis X. The second mounting surface 52 may be adapted to be mounted in a fixed relation relative to the tool guide 2. Thus, an orientation of the first mounting surface 51 relative to the tool guide axis X may be changed, wherein an orientation of the second mounting surface 52 relative to the tool guide axis X is fixed.

The tracking patterns are mounted on the first mounting surface 51 and the second mounting surface 52. Each tracking pattern of the tracking assembly 1 comprises at least one optical marker 511*a*-511*b*, 512*a*-512*b*, 513*a*-513*b* mounted on the first mounting surface 51 and at least one optical marker 511*c*-511*e*, 512*c*-512*e*, 513*c*-513*e* mounted on the second mounting surface 52.

Therefore, as the tracking assembly 1 comprises at least two tracking patterns with different inclinations of visibility axes relative to the reference plane P, each mounting surface 51,52 comprises at least two optical markers having visibility axes with different inclinations relative to the reference plane P.

Furthermore, as the first mounting surface 51 is rotatable around the tool guide axis X and the second mounting surface 52 is fixed, a rotation of the first mounting surface 51 around the tool guide axis X modifies the orientation relative to the tool guide axis X of the optical markers 511*a*-511*b*, 512*a*-512*b*, 513*a*-513*b* which are mounted on the first mounting surface 51, without modifying the orientation relative to the tool guide axis X of the optical markers 511*c*-511*e*, 512*c*-512*e*, 513*c*-513*e* which are mounted on the second mounting surface 52. The orientation of the optical markers 511*a*-511*b*, 512*a*-512*b*, 513*a*-513*b* which are mounted on the first mounting surface 51 varies in a predictable and known way. Therefore, the corresponding tracking patterns may still be accurately detected and localized by the localization system 4.

Such a tracking assembly 1 comprising a rotatable first mounting surface 51 and a fixed second mounting surface 52 may improve the robustness and accuracy of the detection and localization of the tracking patterns.

The first mounting surface 51 may be moved in rotation according to a continuum of orientations around the tool guide axis X, or alternatively according to a discrete number of orientations around the tool guide axis X.

In the example illustrated in FIGS. 4*a* and 4*b*, the tracking assembly 1 comprises three tracking patterns. Each of the three tracking patterns has a range of visibility directed along a visibility axis which has a different inclination relative to the reference plane P. Each tracking pattern comprises five optical markers 511*a*-511*e*, 512*a*-512*e*, 513*a*-513*e*. Among the five optical markers, two optical markers 511*a*-511*b*, 512*a*-512*b*, 513*a*-513*b* are mounted on the first mounting surface 51, and three optical markers 511*c*-511*e*, 512*c*-512*e*, 513*c*-513*e* are mounted on the second mounting surface 52.

For each tracking pattern, all of the optical markers 511*a*-511*b*, 512*a*-512*b*, 513*a*-513*b* which are mounted on the first mounting surface 51 have parallel optical marker visibility axes. The optical markers 511*c*-511*e*, 512*c*-512*e*, 513*c*-513*e* which are mounted on the second mounting surface 52 may have parallel optical marker visibility axes, or alternatively may have visibility axes which are oriented differently around the tool guide axis X.

The first mounting surface 51 may be moved in rotation around the tool guide axis X so that at least one of the optical markers 511*a*-511*b*, 512*a*-512*b*, 513*a*-513*b* which are mounted on the first mounting surface 51 has the same orientation relative to the tool guide axis X as at least one of the optical markers 511*c*-511*e*, 512*c*-512*e*, 513*c*-513*e* which are mounted on the second mounting surface 52. The corresponding detection and localization of the tracking pattern by the localization system 4 is thus improved.

For example, for a given tracking pattern, an optical marker 511*c*, 512*c*, 513*c* mounted on the second mounting surface 52 may be oriented at an angle of approximately 45° around the tool guide axis X relative to a second optical marker 511*d*, 512*d*, 513*d* mounted on the second mounting surface 52, and may be oriented at an angle of approximately 90° around the tool guide axis X relative to a third optical marker 511*e*, 512*e*, 513*e* mounted on the second mounting surface 52.

The tool guide 2 may be adapted to extend from the second mounting surface 52 along the direction of the tool guide axis X.

In this second embodiment, the tracking patterns are mounted on the first and second mounting surfaces 511, 512 of the tracking assembly 1. In particular, the rotatable first mounting surface 51 may not be located on the tool guide 2 itself. Therefore, more space is available around the tool guide 2 itself. Alternatively, both mounting surfaces 51, 52 may correspond to surfaces of the tool guide 2.

The tool guide 2 may comprise a tool channel into which the surgical tool can be inserted, or a tool holder to which the surgical tool can be fixed.

The surgical robotic system may further comprise stabilization means adapted to maintain the tracking assembly 1 in a given position and orientation relative to the tool guide 2 in the absence of solicitation of the tracking assembly 1 in rotation around the tool guide axis X. In other words, the stabilization means allow the tracking assembly, more particularly the rotatable tracking pattern, to stay in a given orientation relative to the tool guide axis X, when it is not solicited in rotation around the tool guide axis X.

The robotic arm 3 and the tracking assembly 1 may both comprise stabilization means which are configured to cooperate with each other in order to maintain the tracking assembly 1 in a given orientation once the rotatable tracking pattern has been rotated to the desired orientation relative to the tool guide axis X, regardless of the orientation of the rotatable tracking pattern.

In a first mode of realization, the tracking pattern is configured to be rotated around the tool guide axis X according to a discrete number of orientations. The stabilization means of the robotic arm 3 may comprise slots and the stabilization means of the tracking assembly 1 may comprise protrusions, the slots and protrusions being regularly and circumferentially spaced around the tool guide 2. During rotation of the tracking assembly 1 around the tool guide axis X, several discrete orientations may be reached, corresponding to the orientations of the rotatable tracking pattern around the tool guide axis X for which the protrusions engage in the slots.

Alternatively, the stabilization means may comprise one or more screws configured to be inserted in or removed from one or more holes of the tracking assembly 1 and/or robotic arm 3. The surgeon may manually take out the at least one screw in order to manually rotate the rotatable tracking pattern, and put the at least one screw back in in order to prevent rotation.

In a second mode of realization, the tracking pattern is configured to be rotated around the tool guide axis X according to a continuum of orientations. The stabilization means of the robotic arm 3 and of the tracking assembly 1 may comprise rough surfaces, the rough surfaces generating sufficient friction when in contact one with the other so as to maintain the tracking pattern in a fixed position relative to the surgical robotic system once it has been rotated to the desired orientation relative to the tool guide axis X.

The surgical robotic system may further comprise:

a reference tracking assembly 5, a localization system 4 adapted to detect and localize the reference tracking assembly 5 and the tracking assembly 1 when the localization system 4 is within a range of visibility of at least one tracking pattern of the tracking assembly 1, the localization system 4 being adapted to determine a position and an orientation of the tracking assembly 1 relative to a position and an orientation of the reference tracking assembly 5.

The reference tracking assembly 5 may be adapted to be positioned and/or oriented in a fixed relationship relative to a surgical target. Thus, localizing the tracking assembly 1 relative to the reference tracking assembly 5 allows the localization of the tracking assembly 1 relative to the surgical target.

The reference tracking assembly 5 may be attached to an anatomical structure, for example the body of the patient, and may be placed next to the surgical target. The reference tracking assembly 5 may comprise one or more tracking patterns, each tracking pattern comprising at least three optical markers.

The reference tracking assembly 5 is positioned so that the localization system 4 is within a range of visibility of at least one tracking pattern of the reference tracking assembly 5. For example, the reference tracking assembly 5 may be positioned on the patient before the surgical act. Thus, the reference tracking assembly 5 may be detected and localized at all times during surgery by the localization system 4.

A method for aligning a tool guide 2 of a surgical robotic system as described above with a surgical target axis comprises the following steps:

S1: detecting and localizing, by the localization system 4:

(a) a reference tracking assembly 5 attached to an anatomical structure in a determined fixed position and orientation relative to the surgical target axis, and (b) at least one tracking pattern of the tracking assembly 1, if necessary, by rotating at least one tracking pattern of the tracking assembly 1 around the tool guide axis X, S2: determining a position and/or orientation of the tool guide 2 relative to the surgical target axis, based on the detection and localization of the tracking assembly 1 relative to the reference tracking assembly 5 performed in step S1 and on the position and orientation of the reference tracking assembly 5 relative to the surgical target axis, S3: moving the robotic arm 3 to adjust the position and/or orientation of the tool guide 2 to align the tool guide axis X with the surgical target axis.

The position and/or orientation of the surgical target axis may be defined before or during surgery and correspond to an absolute surgical target axis position and/or orientation, which may be expressed in a coordinate system attached to the patient.

The position and/or orientation of at least one tracking pattern of the tracking assembly 1 is determined relative to the position and orientation of the reference tracking assembly 5. Thus, the position and orientation of the tracking assembly 1 relative to the surgical target may be deduced.

The robotic arm 3 is manipulated in step S3 in order to align the tool guide 2 with the surgical target axis. Then, the position and/or orientation of the tool guide 2 may respectively correspond to the position and/or orientation of the surgical target axis. When the tool guide 2 is aligned with the surgical target, the localization of the tool guide 2 may correspond to the localization of the surgical target axis. More particularly, a localization of a tool stop located on a proximal face of the tool holder, may correspond to the localization of the surgical target. The localization of the tool stop defines a maximum depth of insertion for the tool.

For example, the user may have to implant one or several screws into one or several vertebrae, femoral neck or fractured bone.

The tool guide may be used as a drill guide. The tool guide allows positioning of the drill on a vertebra to be drilled and maintains the drill at a desired orientation and/or depth relative to the vertebra.

One or several surgical targets may be defined for one surgical procedure. The robotic arm of the surgical robotic system must be moved during surgery in order to sequentially place the tool holder relative to each of the defined surgical targets.

The steps of the method may be performed successively for every surgical target. The reference tracking assembly 5 may be fixed throughout the surgical procedure. The tool guide 2 is first aligned with a first surgical target axis, by a corresponding detection of at least one tracking pattern and movement of the robotic arm 3. Then the tool guide 2 is aligned with a next surgical target axis, by a corresponding detection of at least one tracking pattern and movement of the robotic arm 3. If necessary, the rotatable tracking pattern is rotated around the tool guide axis X. Rotation of the rotatable tracking pattern around the tool guide axis X may be predetermined before or during surgery according to the number, positions and orientations of the one or several surgical targets to be reached. Thus, complex surgical procedures may be performed.

The step S1, more particularly the step S1(b) of detecting and localizing at least one tracking pattern of the tracking assembly 1, may comprise the following steps:

S11: acquiring an image by the localization system 4,

S12: if no tracking pattern is detected by the localization system 4 on the basis of the acquired image, rotating at least one tracking pattern of the tracking assembly 1 around the tool guide axis X until the localization system 4 detects at least one tracking pattern of the tracking assembly 1, S13: detecting and localizing at least one of the at least one detected tracking pattern of the tracking assembly 1 by the localization system 4.

The image acquired in step S11 may correspond to a binary image in which the value 1 corresponds to a detected optical marker, and the value 0 corresponds to no detected optical marker.

At least one tracking pattern of the tracking assembly 1, which corresponds to the rotatable tracking pattern, may be rotated around the tool guide axis X in step S12. Such a rotation of the rotatable tracking pattern around the tool guide axis X may be needed for example if, in a given position and orientation of the surgical robotic system, the localization system 4 is within the range of no tracking pattern at all. The rotatable tracking pattern is then rotated around the tool guide axis X until the localization system 4 is within the range of at least one tracking pattern.

This method allows a precise positioning and orientating of the tool guide 2, so that the position and orientation of the tool may coincide with the defined surgical target, in a wide range of positions and orientations of the surgical robotic system.

The method may further comprise a step of calibration of the localization system 4. The calibration step may comprise a definition of the spatial relationship between the optical markers 11a-13d of the tracking patterns and the tool guide axis X to be aligned with the surgical target axis. The calibration step may be performed before the start of the surgical procedure.

The spatial relationship between the optical markers 11a-13d of the rotatable tracking pattern and the tool guide axis X is unchanged by the rotation of the rotatable tracking pattern around the tool guide axis X. Thus, the tracking pattern may be rotated around the tool guide axis X without modifying the detection and localization of the tool guide axis X by the localization system 4. Indeed, the localization system 4 may detect and localize the optical markers 11a-13d with respect to the tool guide axis X in the same way, regardless of the tracking pattern's orientation around the tool guide axis X.

Figures 5A, 5B:
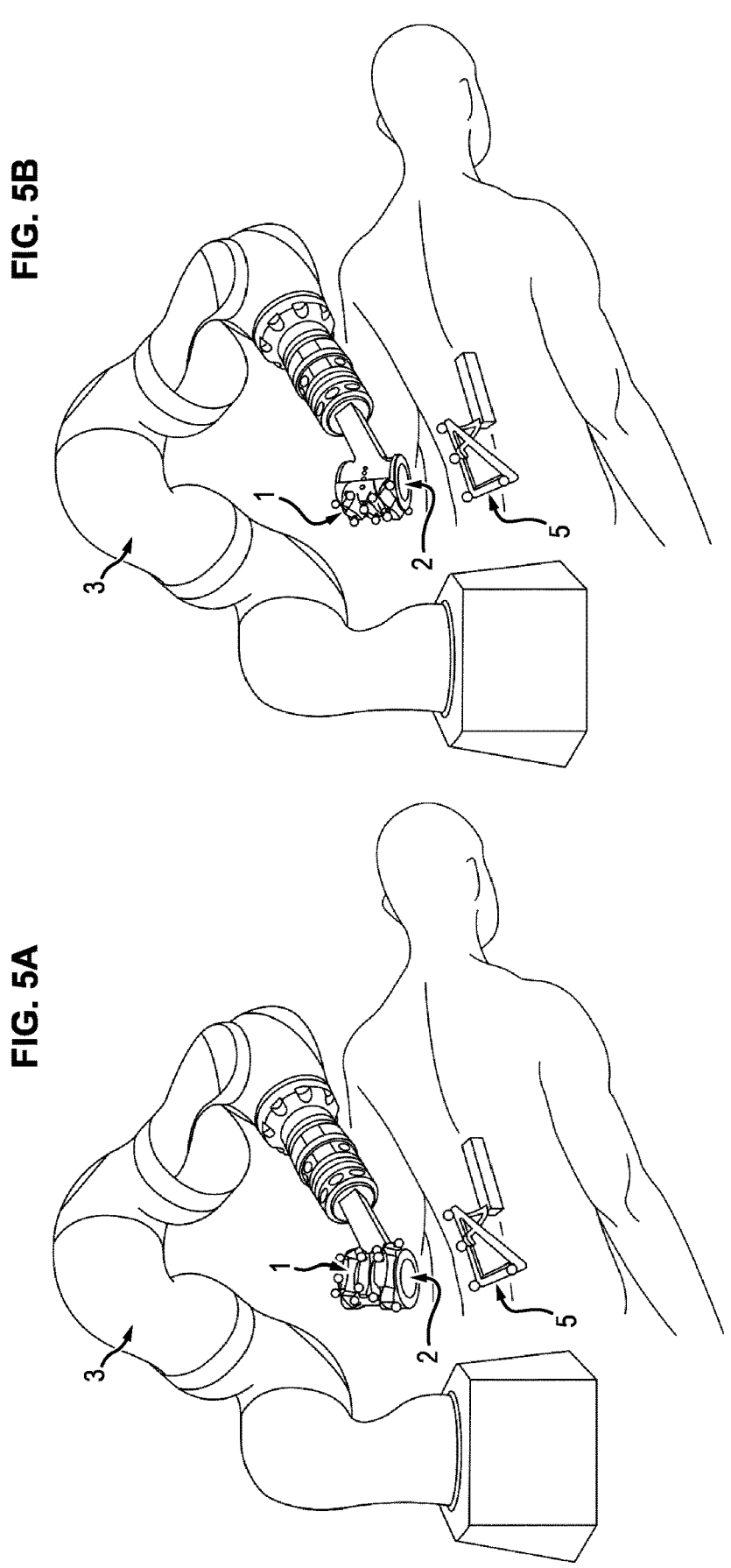
FIGS. 5a and 5b are perspective views of a surgical robotic system according to an embodiment of the invention.

FIGS. 5a and 5b illustrate examples of a surgical robotic system with a tracking assembly 1 having two different orientations around the tool guide axis X. The tracking assembly 1 of FIGS. 5a and 5b is rotatable as a whole around the tool guide axis X.

Figures 6A, 6B:
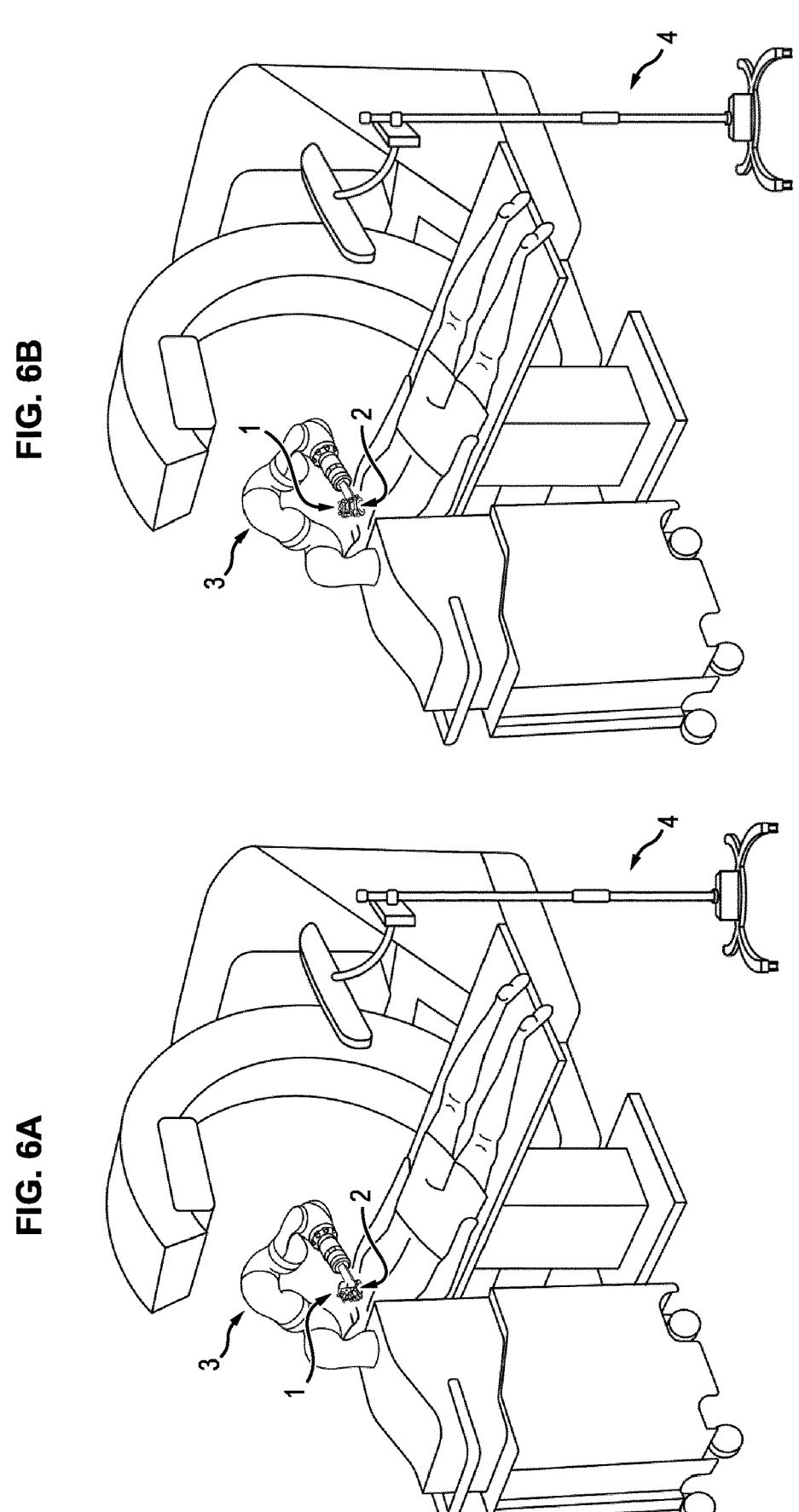
FIG. 6a is a perspective view of a surgical robotic system according to an embodiment of the invention, the localization system being outside the range of visibility of all of the tracking patterns of the tracking assembly.
FIG. 6b is a perspective view of a surgical robotic system according to an embodiment of the invention, the localization system being within the range of visibility of at least one tracking pattern of the tracking assembly.

FIGS. 6a and 6b also illustrate examples of a surgical robotic system with a tracking assembly 1 having two different orientations around the tool guide axis X. The tracking assembly 1 of FIGS. 6a and 6b is rotatable as a whole around the tool guide axis X.

In FIG. 6a, the localization system 4 is outside the range of visibility of all of the tracking patterns of the tracking assembly 1. Thus, the tracking assembly 1 should be rotated around the tool guide axis X in order for the localization system 4 to accurately detect and localize it. In FIG. 6b, the localization system 4 is within the range of visibility of at least one tracking pattern of the tracking assembly 1. Thus, the tracking assembly 1 is adapted to be accurately detected and localized by the localization system 4.

The surgical robotic system may further comprise actuating means configured to rotate the at least one rotatable tracking pattern around the tool guide axis X. The surgical robotic system may further comprise a control unit adapted to control the actuating means and/or change a position and/or orientation of the robotic arm 3.

In a first example of realization, the step of rotating at least one tracking pattern of the tracking assembly 1 around the tool guide axis X is performed manually by a user.

The actuating means may comprise motorized means, such as electric motors, as well as a command means, such as button, actionable by the surgeon. The surgeon may manually continuously press the button, for example during the surgical procedure, in order for the motors to rotate the at least one rotatable tracking pattern, and release the button in order to stop action of the motors and thus stop rotation of the at least one rotatable tracking pattern.

In a second example of realization, the step of rotating at least one tracking pattern of the tracking assembly 1 around the tool guide axis X is performed automatically by motorization means. As soon as one pattern is visible, the motor is adjusted continuously to ensure that said pattern remains visible during the motion of the robot, or that the other pattern becomes visible and remains visible.

The motorization means may be controlled by the control unit according to the result of the detection of a tracking pattern by the localization system 4. In other words, the rotation of the rotatable tracking pattern is servo-controlled on the result of the detection of the tracking assembly 1 by the localization system 4.

For example, for a given position and orientation of the robotic arm 3, if the localization system 4 does not detect any tracking pattern of the tracking assembly 1 (negative detection), the control unit may command actuation of the motorization means in order to rotate the rotatable tracking pattern by a predetermined number of degrees around the tool guide axis X. For example, in the case of a negative detection, the control unit may command rotation of the rotatable tracking pattern by around 45°. Rotation of the rotatable tracking pattern is thus incremental.

If the localization system 4 detects at least one tracking pattern (positive detection), the control unit may command a stop of the motorization means rotating the rotatable tracking pattern around the tool guide axis X.

Alternatively, the control unit may determine whether or not the accuracy of the detection and localization of the detected tracking pattern is sufficient. For example, if the localization system 4 is close to the borders of the range of visibility of a tracking pattern, the localization system 4 may detect a tracking pattern, but not accurately localize it (positive but not optimal detection). In this case, the control unit may command a further rotation of the rotatable tracking pattern, in order for the localization system 4 to be optimally positioned within the range of visibility of the tracking pattern to be detected and localized.

The commanded rotation of the rotatable tracking pattern in the case of a positive but not optimal detection may be the same or different from the commanded rotation of the rotatable tracking pattern in the case of a negative detection. For example, the control unit may command a rotation of the rotatable tracking pattern of around +/−10° in the case of a positive but not optimal detection, and of around +/−45° in the case of a negative detection.

Alternatively, the control unit may command actuation of the motorization means in order to rotate the rotatable tracking pattern in a synchronized manner with the movements of the robotic arm 3. Therefore, the tracking assembly 1 always stays in an optimal position with regards to its localization by the camera.

Once the tracking assembly 1 is detected and localized relative to the surgical target, the robotic arm 3 is moved. Actioning of the robotic arm 3 may be performed manually by the surgeon or an assistant. Alternatively, actioning of the robotic arm 3 may be performed automatically, for example may be performed by the control unit commanding further motorized means of the surgical robotic system. The further motorized means are adapted to automatically change a localization of the robotic arm 3 in order to position and orient the tool guide 2, which is mounted on the robotic arm 3, on the surgical target, that is to say in order to align the tool guide 2 with the surgical target axis. The localization of the tool guide 2 is determined from the localization of the tracking assembly 1, as described above.

The invention claimed is:

1. A tracking assembly for a surgical robotic system, the surgical robotic system comprising a tool guide extending substantially coaxially to a tool guide axis, the tracking assembly being adapted to be mounted on the surgical robotic system, wherein the tracking assembly comprises at least two tracking patterns, each tracking pattern comprising at least three optical markers, wherein at least one of said at least two tracking patterns is adapted to be rotatably mounted relative to the tool guide so as to be moveable in rotation around the tool guide axis, wherein each of said at least two tracking patterns defines a cone of visibility associated to the tracking pattern, the cone of visibility being substantially directed along a visibility axis, wherein an inclination of the visibility axis of a first tracking pattern relative to a reference plane normal to the tool guide axis is different from an inclination of a second tracking pattern relative to the reference plane, wherein the tracking assembly is adapted to be detected and localized by a localization system when the localization system is within the cone of visibility of at least one tracking pattern of the tracking assembly.

2. The tracking assembly of claim 1, wherein each optical marker is a reflective disk.

3. The tracking assembly of claim 1, wherein each optical marker is a reflective sphere.

4. The tracking assembly of claim 1, wherein each optical marker is an active marker.

5. The tracking assembly of claim 1, further comprising at least two additional tracking patterns, wherein each of said at least two additional tracking patterns defines a cone of visibility associated to the respective additional tracking pattern, the cone of visibility being substantially directed along a visibility axis, wherein an inclination relative to the reference plane of the visibility axis of a first additional tracking pattern is identical to an inclination relative to the reference plane of the visibility axis of a second additional tracking pattern, and wherein an orientation relative to the tool guide axis of the visibility axis of the first additional tracking pattern of the tracking assembly is different from an orientation relative to the tool guide axis of the visibility axis of the second additional tracking pattern of the tracking assembly.

6. A surgical robotic system, comprising:

the tracking assembly of claim 1;

a robotic arm comprising the tool guide extending substantially coaxially to the tool guide axis normal to the reference plane, the tracking assembly being adapted to be mounted on the robotic arm of the surgical robotic system.

7. The surgical robotic system of claim 6, wherein the tool guide of the robotic arm is substantially in the shape of a hollow revolution cylinder extending around the tool guide axis, the tool guide comprising an outer wall and an inner wall, wherein the tracking assembly is adapted to be mounted on the outer wall of the tool guide so that all tracking patterns of the tracking assembly are movable in rotation around the tool guide axis, and wherein the inner wall of the tool guide is adapted to guide a translation of a surgical tool along the tool guide axis.

8. The surgical robotic system of claim 6, wherein the tracking assembly comprises at least a first mounting surface and a second mounting surface, wherein the first mounting surface is adapted to be rotatably mounted relative to the tool guide so as to be moveable in rotation around the tool guide axis and the second mounting surface is adapted to be mounted in a fixed relation relative to the tool guide, and wherein each tracking pattern of the tracking assembly comprises at least one optical marker mounted on the first mounting surface and at least one optical marker mounted on the second mounting surface.

9. The surgical robotic system of claim 6, further comprising stabilization means adapted to maintain the tracking assembly in a given position and orientation relative to the tool guide in the absence of solicitation of the tracking assembly in rotation around the tool guide axis.

10. The surgical robotic system of claim 6, further comprising:

a reference tracking assembly, a localization system adapted to detect and localize the reference tracking assembly and the tracking assembly when the localization system is within a cone of visibility of at least one tracking pattern of the tracking assembly, the localization system being adapted to determine a position and an orientation of the tracking assembly relative to a position and an orientation of the reference tracking assembly.

11. A method for aligning a tool guide of a surgical robotic system according to claim 10 with a surgical target axis, comprising the following steps:

S1: detecting and localizing, by the localization system:

(a) a reference tracking assembly attached to an anatomical structure in a determined fixed position and orientation relative to the surgical target axis, and (b) at least one tracking pattern of the tracking assembly, if necessary, by rotating at least one tracking pattern of the tracking assembly around the tool guide axis, S2: determining a position and/or orientation of the tool guide relative to the surgical target axis, based on the detection and localization of the tracking assembly relative to the reference tracking assembly performed in step S1 and on the position and orientation of the reference tracking assembly relative to the surgical target axis, S3: moving the robotic arm to adjust the position and/or orientation of the tool guide to align the tool guide axis with the surgical target axis.

12. The method of claim 11, wherein the step S1 comprises the following steps:

S11: acquiring an image by the localization system,

S12: if no tracking pattern is detected by the localization system on the basis of the acquired image, rotating at least one tracking pattern of the tracking assembly around the tool guide axis until the localization system detects at least one tracking pattern of the tracking assembly, S13: detecting and localizing at least one of the at least one detected tracking pattern of the tracking assembly by the localization system.

13. The method of claim 12, wherein rotating at least one tracking pattern of the tracking assembly around the tool guide axis is performed manually by a user.

14. The method of claim 12, wherein rotating at least one tracking pattern of the tracking assembly around the tool guide axis is performed automatically by motorization means, the motorization means being controlled according to the result of the detection of a tracking pattern by the localization system.

\* \* \* \* \*